(12) United States Patent
Chawan

(10) Patent No.: US 7,053,066 B2
(45) Date of Patent: *May 30, 2006

(54) FOOD COMPOSITION AND WEIGHT LOSS METHOD FOR TREATING OBESITY

(75) Inventor: Dhyaneshwar Bhujangarao Chawan, Liverpool, NY (US)

(73) Assignee: Heartland Health Solutions, LLC, Brentwood, TN (US)

( * ) Notice: Subject to any disclaimer, the term of this patent is extended or adjusted under 35 U.S.C. 154(b) by 247 days.

This patent is subject to a terminal disclaimer.

(21) Appl. No.: 10/226,473

(22) Filed: Aug. 23, 2002

(65) Prior Publication Data

US 2004/0038909 A1 Feb. 26, 2004

(51) Int. Cl.
*A61K 31/715* (2006.01)

(52) U.S. Cl. .................. 514/54; 536/123.1; 536/123.12

(58) Field of Classification Search .................. 514/54; 536/123.1, 123.13, 123.12
See application file for complete search history.

(56) References Cited

U.S. PATENT DOCUMENTS

| | | | |
|---|---|---|---|
| 4,237,118 A | 12/1980 | Howard | |
| 4,379,174 A * | 4/1983 | Radlove | 426/554 |
| 4,393,049 A | 7/1983 | Horrobin | |
| 4,784,861 A | 11/1988 | Gori | |
| 5,055,460 A | 10/1991 | Friedlander | |
| 5,246,723 A | 9/1993 | Kameyama et al. | |
| 5,470,839 A | 11/1995 | Laughlin et al. | |
| 5,695,803 A | 12/1997 | Sharp et al. | |
| 5,759,607 A * | 6/1998 | Chawan et al. | 426/557 |
| 5,776,887 A | 7/1998 | Wibert et al. | |
| 5,783,603 A | 7/1998 | Majeed et al. | |
| 5,851,531 A | 12/1998 | Lazarus | |
| 5,855,949 A | 1/1999 | McLean | |
| 5,904,926 A | 5/1999 | Slavin | |
| 5,989,574 A | 11/1999 | Slavin | |
| 6,191,117 B1 | 2/2001 | Kozachuk | |
| 6,210,702 B1 | 4/2001 | Samman | |
| 6,224,873 B1 | 5/2001 | Jones | |

OTHER PUBLICATIONS

Kaneuchi et al. (JP 05186356 (Abstract Only)) (Abstract Sent).*
Fujita et al. (JP 359130158A), Jul. 26, 1984 (Abstract only) (Abstract Sent).*
Watabe (JP 04063560 A2, Feb. 28, 1992 (Abstract Only)). (Abstract Sent).*
Carroll, et al. Dietary Fiber and cholesterol metabolism in rabbits and mts, Am. J.. F Clinical Nutrition, vol. 31, 5203-5207 1978.
Bornet, et al. Instit and Glycemic Responses in Healthy Hormones to nature starches, Am. J. if clinical Nutrition, vol. 50, 315-323 1989.
Ford Additives Series No. 5, Joint FAO/Wito Expert Committee on Food Additives, Jun. 25-Jul. 4, 1973.
Resistant Starches, information from natural starch and chemical Company.
Englyst, et al. Digestion of Polysaccharides of potato in the small intestine of man, Am. J. Clin. Nutrition, vol. 45, 423-431 1987.

* cited by examiner

*Primary Examiner*—Samuel Barts
(74) *Attorney, Agent, or Firm*—Dennis H. Rainear

(57) ABSTRACT

The invention relates to a method for treating overweight persons or patients with obesity using a food composition able to control the release of glucose into the patient's blood. This is achieved by the introduction into the food composition of a therapeutically effective amount of an additive, such as propylene glycol alginate (PGA) or other hydrophilic agent or pharmaceutically acceptable salts thereof, which reduces the cooking losses and enhances the starch cell wall membrane to thereby slow the enzymatic hydrolysis of the starch by insulin. The result is a steady state release of glucose and a net reduction in the release of blood glucose (glycemic index) relative to release of glucose observed in an overweight or obese patient having consumed a food composition without propylene glycol alginate, whereby the patient experiences a loss in body weight.

7 Claims, No Drawings

FOOD COMPOSITION AND WEIGHT LOSS METHOD FOR TREATING OBESITY

FIELD OF INVENTION

The invention relates to a method for treating overweight individuals or patients with obesity using a food composition able to control the release of glucose into the patient's blood. This is achieved by the introduction into the food composition of a hydrophilic food grade agent, such as propylene glycol alginate, which reduces the cooking losses and enhances the starch cell wall membrane to thereby slow the enzymatic hydrolysis of the gelatinized starch. The result is a steady state release of glucose and a net reduction in the blood glucose (glycemic index) relative to blood glucose observed in an overweight or obese patient having consumed a comparable food composition without propylene glycol alginate.

BACKGROUND OF THE INVENTION

Obesity is a serious health threat throughout the industrialized nations. It can lead to significant illnesses and premature death. Unfortunately, its rate of incidence is increasing. Obesity is a major disorder affecting as much as one third of the North American population. Several studies have shown that such individuals are at increased risk in developing cardiovascular disease (hypertension and hypercholesterolemia), diabetes and several types of cancer. The effective treatment of obesity, however, remains a largely unachieved goal. Existing pharmacotherapeutic approaches to weight loss involve the use of amphetamine-based agents such as amphetamine, diethylpropion, mazindol and fenfluramine which act directly on the CNS to lower food intake by modulating dopaminergic, adrenergic and/or serotonergic mechanisms. Although weight loss can be achieved with such agents, their use is restricted due to CNS side-effects, potential addiction liability and the production of tolerance to their actions, with chronic administration leading to potential depression, vestibular disturbances, hallucinations and addiction, as well as interference with the actions of other drugs such as MAO inhibitors and antihypertensives. There is also a subpopulation of obese patients that is refractory to present anorectic drug treatments. The medical need is high for an effective agent which overcomes the above disadvantages of existing therapies. Of particular need are agents which act by alternative mechanisms to modulate food intake and/or metabolism.

When people eat, their bodies turn the Carbohydrates in food into glucose (sugar) to use as fuel. In healthy people, insulin helps the glucose get into the cells. In people with obesity, glucose builds up in the blood beyond a normal or healthy level. In the absence of low insulin levels (as in obese patients) the blood glucose level rises above the safe levels.

Many patents teach and claim pharmaceutical or food compositions for the treatment of obesity or achieving weight reduction. U.S. Pat. No. 6,210,702 teaches a bread weight loss composition.

U.S. Pat. No. 5,055,460 teaches a method for producing human weight loss comprising administering an effective amount of aspirin, caffeine and ephedrine.

U.S. Pat. No. 4,237,118 teaches a dietary supplement of minerals vitamin and skimmed milk.

U.S. Pat. No. 4,393,049 teaches treating obesity by the administration of gamma-linolenic acid.

U.S. Pat. No. 5,989,574 teaches weight reduction in humans by administering a composition comprising zinc acetate and copper.

U.S. Pat. No. 5,783,603 teaches appetite suppression by administering to the patient a diet containing potassium hydroxycitric lactone.

U.S. Pat. No. 5,851,531 teaches a method of inducing weight loss by administering to a patient a lectin selected from pokeweed mitogen and Momordica lectin.

U.S. Pat. No. 6,191,117 teaches a method for treating obesity comprising administering a compound whose mechanism of action includes antagonism of the kainite and/or AMPA receptor.

U.S. Pat. No. 4,784,861 teaches an ingestible formulation of fiber for absorbing water for weight control.

U.S. Pat. No. 5,904,926 teaches a method for effecting weight reduction in a patient by administering to the patient zinc acetate and copper gluconate.

U.S. Pat. No. 6,224,873 teaches a method of regulation of appetite and body weight with materials derived from citrus plants.

U.S. Pat. No. 5,776,887 teaches a nutritional product having controlled absorption of carbohydrate. The product taught in U.S. Pat. No. 5,776,887 comprises protein, fat, carbohydrate, fiber and disaccharides.

U.S. Pat. No. 5,470,839 teaches an enteral diet and method for providing nutrition to a patient based on low carbohydrates, high fat, plus protein.

U.S. Pat. No. 5,246,723 teaches a food material comprising a farinaceous substance and a fatty acid compound to achieve a slowed absorption of said food material.

U.S. Pat. No. 5,855,949 teaches a dietary system high in oil intake using carbohydrates, oil, and hormones to reduce fat storage and stimulate the glucagon-driven pathway.

U.S. Pat. No. 5,695,803 teaches nutritional products containing acid treated starches.

U.S. Pat. No. 5,759,607 teaches the use of propylene glycol alginate to improve the texture of food compositions, particularly pasta.

No correlation of use of propylene glycol alginate and obesity reduction is taught or implied in the references discussed herein.

What is needed is a dietary treatment for patients suffering from obesity which reduces the glycemic index of foods for said patients. The dietary treatment should supply nutrition to an obese patient while substantially reducing said patient's blood glucose level, preventing weight gain, and promoting body weight loss. A dietary treatment for patients with obesity which is low in fat and or cholesterol would also be desirable.

SUMMARY OF THE INVENTION

The present invention is directed to a food composition, and a dietary method comprising said composition, for treating overweight individuals and patients with obesity.

This invention provides a method that controls the glucose release initiated by enzymatic action, said method comprising the step of enterally administering to an overweight or obese patient a meal comprising a blood glucose level reducing amount of a food composition comprising at least 0.01 weight percent propylene glycol alginate (also referred to herein as "PGA"), or pharmaceutically acceptable salts thereof.

Thus, in an embodiment, the present invention is directed to a method for controlling during starch hydrolysis the membrane structure of a starch granule in a food composition for an overweight or obese person by the incorporation into said food composition of a therapeutically effective amount of PGA or other hydrophilic agent or pharmaceutically acceptable salts thereof.

In another embodiment of the present invention is presented a method of reducing the glycemic index in a patient suffering obesity or abnormally high blood glucose levels, said method comprising the step of including in the diet of said obese patient a glycemic index reducing amount of a food composition comprising at least 0.01 wgt % of propylene glycol alginate or pharmaceutically acceptable salts thereof.

The invention further relates to a method of reducing the glycemic index in a patient suffering obesity, said method comprising the step of including in the diet of said obese patient a glycemic index reducing amount of a food composition containing at least 0.01 wgt % of one or more materials selected fom the group consisting of glycerol, sugar alcohol, starch hydrolysate, corn syrup, dextrose syrup, glycerol monostearate, sodium stearoyl lactylate, D-glucose 3-stearate, methyl alpha-D-glucoside 6-stearate, sucrose monostearate, sorbitan tetrastearate, stearoyl-2-lactylate, sodium stearoyl fumarate, polyoxyethylene stearate, and stearyl monoglyceride citrate.

The invention further relates to pasta, or other food composition, which contains a therapeutically effective amount of propylene glycol alginate or pharmaceutically acceptable salts thereof for use in the treatment of obesity.

The invention also relates to the use of propylene glycol alginate or pharmaceutically acceptable salts thereof in the manufacture of a pasta foodstuff, or other food composition, for use in the treatment of obesity.

In another embodiment, the present invention relates to a method of inducing weight loss in in need thereof comprising administering to said people a food composition comprising propylene glycol alginate or pharmaceutically acceptable salts thereof, in an amount effective to induce a decline in blood glucose level in said and continuing said administering step to maintain the decline in blood glucose level until a loss of weight is attained. Another aspect of the present invention is a method for treating obesity or excessive weight gain in which comprises administering to people in need of weight reduction or weight control a therapeutically effective amount of propylene glycol alginate or a pharmaceutically acceptable salt thereof.

In a preferred embodiment, the food composition of the present invention is a pasta product.

According to the present invention, patients suffering with obesity or abnormally high blood glucose levels can, in a controlled or steady state manner, reduce their blood sugar level by consuming a meal comprising a starch-containing cereal grain food composition, such as a pasta product, which contains a therapeutically effective amount of propylene glycol alginate or pharmaceutically acceptable salts thereof (hereinafter collectively "PGA").

This invention also provides a method for providing nutrition to an obese or overweight patient while substantially reducing said patient's blood glucose level, said method comprising the step of enterally administering to the obese patient a meal comprising a blood glucose level reducing amount of a food composition comprising at least 0.01 weight percent propylene glycol alginate or pharmaceutically acceptable salts thereof.

The invention further provides a method for suppressing appetite in a patient in need of such effect comprising administering to said patient an appetite suppressing effective amount of a food composition comprising propylene glycol alginate or pharmaceutically acceptable salts thereof.

In addition, the invention provides a method for substantially reducing the blood glucose level and/or body weight in an overweight or obese person, said method comprising the step of enterally administering to the person a food composition prepared by a method comprising;

(a) preparing a food composition consisting of wheat, tapioca, barley, oat, potato, rice or corn flour or mixture thereof, water and at least 0.01 weight percent propylene glycol alginate or pharmaceutically acceptable salts thereof;

(b) cooking said food composition by, for example, placing in boiling water for a time sufficient to increase the percent weight gain due to hydration relative to a comparable food composition without propylene glycol alginate similarly cooked; and (c) consumption of said food composition by said person.

The PGA-containing food composition products of the present invention have been designed to exhibit reduced cooking losses, an indirect test to confirm the reduction in glycemic index compared to the analogous product without PGA. When starch-containing food is cooked in boiling water, there has long been a problem with a cooking loss of a certain percentage of mass from the food coming out of the food and remaining in the cooking water.

Functionality of PGA is measured herein indirectly as reduction in solids lost in cooking water. This may be attributable to propylene glycol alginate complexation with the starch cell wall membrane, making it elastic thus preventing rupture and release of the gelatinized contents (such as amylose and amylopectin) of the starch cell. The gelatinized starch cell contents are randomly hydrolyzed to glucose by the digestive enzymes (Amylases).

It has been discovered in the present invention that by reducing the cooking losses of starchy food containing PGA, a food composition can be produced which, when consumed by a patient suffering obesity or abnormally high blood glucose levels, will result in a blood glucose level reduction in said patient, relative to the blood glucose level of an obese patient who has consumed comparable food not containing PGA. As a result, the obese patient experiences a reduction in body weight. Therefore, the present invention provides a method for weight reduction.

During cooking of a starch-containing food, the starch contained in the food is 'gelatinized'. This is an essential step that helps enzymes to break down the starch to glucose. Gelatinization of starch particles involves three main steps 1. hydration, 2. swelling, and 3. release of primarily amylose (a straight chain glucose polymer), and amylopectin (a branched chain glucose polymer). The ratio of amylose to amylopectin released can vary depending on the source of the starch, such as corn, rice, oats, barley, tapioca, wheat, etc.

In normally healthy people who are not overweight, the glucose generated by the random enzyme hydrolyses is transported into the muscle across the cell wall by the hormone insulin. Insulin is responsible for maintaining optimum level (70 to 120 milligrams/deciliter) of glucose in blood. It has been discovered in the present invention that by reducing the cooking losses of pasta containing PGA or one or more of certain other hydrophilic agents, a food composition can be produced which, when consumed by a patient suffering obesity or abnormally high blood glucose levels, will result in a blood glucose level reduction in said obese patient, relative to the blood glucose level of an obesity patient who has consumed conventional pasta not containing PGA or said hydrophilic agent(s).

It has also been discovered in the present invention that the incorporation of certain hydrophilic agents, such as but not limited to PGA, into a food composition containing starch granules can control the hydrolysis rate of said starch granules. This control on the rate of starch hydrolysis produces a steady state release of glucose over the several hour period following consumption of said food composition. By this manner, the blood glucose levels and/or the glycemic index of the food can be regulated, and total body weight can be reduced.

DETAILED DESCRIPTION OF THE INVENTION

By "food composition" herein is meant any starch-containing food product, such as but not limited to tapioca, potato, wheat, rice, barley, oat, or corn, or cereal grain (e.g. farinaceous), and mixtures thereof. These can be consumed by the obese patient in the form of pasta, noodles, macaroni, spaghetti, rigatoni, ravioli, fettuccini, couscous, pancakes, waffles, breads, pizza, tortillas, taco shells, and the like. Also included as food compositions here are cooked potatoes, breakfast cereals, pastries, rice cakes, dough-wraps, and the like.

By "obese" and/or "obesity" and/or "overweight" herein are meant an individual whose body weight is twenty percent (20%) or more above the level considered by the U.S. Public Health Department, and/or similar organizations to be normal or healthy for the individual's age and gender.

By "therapeutically effective amount" herein is meant an amount sufficient to achieve the desired effect of body weight reduction. In this invention, that generally means an amount equal to or greater than 0.01 weight percent in a food composition.

The word "people/person" and "patient" are used interchangeably herein to refer to individuals who are overweight, whether under a physician's care or not.

Cooking losses in starch-containing foods, such as pasta, have been observed for a long time. The loss is seen by the consumer as a cloudy or milky appearance in the boiling water drained off the cooked food. In this cloudy drain water is material extracted from the food. This loss in mass of the cooked food product can be as high as 15 weight percent. The material which is extracted into the boiling water, drained, and thus lost to the consumer is primarily amylose and amylopectin, but also contains vitamins and minerals both natural and exogenous.

It has been discovered in the present invention that the retention of such materials inside the gelatinized (cooked) starch cell of a food composition containing an effective amount of PGA can be extremely beneficial to patients suffering from obesity who consume said food composition.

The retention of the desirable amylose and amylopectin inside the starch particle of the cooked food, such as pasta, containing PGA, and the desirable resistance of the starch cell wall in the cooked food to rupturing, measured as a reduction of cooking losses, can be achieved according to the present invention by means of incorporating the PGA into the food composition before the food composition is cooked, then cooking said food composition.

One preferred method of cooking said food composition is the immersion in boiling water, or exposure to sufficient steam, or microwaving to gelatinize the starch granules in the cells of said food composition.

PGA can readily be incorporated into the food compositions of the present invention by the methods taught in U.S. Pat. No. 5,759,607 the teachings of which are fully incorporated herein by reference.

One feature of the present invention is the ability to make the gelatinized starch in the food composition less accessible for enzyme attack. The presence of PGA in the food is believed to make the starch cell membrane stronger, which minimizes or prevents the rupture or breakdown of the starch cell wall, a large contributor to cooking loss. It is believed, but the inventor does not wish to be limited to the theory that, the PGA present in the food composition of the present invention, lets the starch cell membrane expand to allow the enzyme to enter. The result is the improved control of the enzymatic starch hydrolysis, thereby creating a steady state glucose release into the blood. This has the effect of reducing the glycemic index of the food which the patient is consuming.

As a result of this invention, patients suffering from obesity or abnormally high blood glucose levels who consume food compositions of this invention can have their insulin treatments reduced, or can be removed from insulin dependence because the food compositions of the present invention when consumed achieve the controlled starch hydrolysis for steady state glucose release.

Thus, the invention further relates to a meal for a person with obesity or an abnormally high blood glucose level containing a food selected from the group consisting of wheat, oat, barley, tapioca, potato, rice and corn, and further containing an amount of propylene glycol alginate equal to or greater than 0.01 weight percent of said food.

In addition, the present invention relates to a method for substantially reducing the body weight of an obese person, said method comprising the step of enterally administering to the obese person a food composition prepared by a method comprising;

(a) preparing a food composition containing wheat, tapioca, barley, oat, potato, rice, or corn flour, or mixture thereof, water and at least 0.01 weight percent propylene glycol alginate; and (b) cooking said food composition by, for example, placing in boiling water for a time sufficient to increase the percent weight gain due to hydration relative to a similarly cooked food composition without propylene glycol alginate.

EXPERIMENTAL

Cholesterol-free Product and Recipe
Product Preparation Procedure:
Ingredients:

| | | |
|---|---|---|
| Sliced Onions/Mixed Vegetables | One Cup | 160 grams |
| Chopped Ginger | One tsp | 4 grams |
| Chopped Hot Green Peppers | One tsp | 3.5 grams |
| Salt | One tsp | 7 grams |
| Oil (Canola or Olive oil) | Two TBS | 22 grams |
| Black Mustard Seed | ¼ tsp | 1 gram |
| Urad Dal (Lentil) | One tsp | 5 grams |
| Water | Two cups | 500 grams |
| (plus flavor if desired) | | |
| Couscous-like Durum wheat product | | 125 grams |

Procedure:

In a two-quart saucepan heat the oil (or butter or margarine). Add black mustard seed & wait until crackles. Add Urad dal and let brown lightly. Wait until mustard 'crackles'.

Add onions and saute until onions are softened/transparent (when veggies are used no sauteing is needed). Add salt. Add water. Mix well and bring the contents to boil. Shut-off the heat. Add the couscous-like product. Mix well until all the water is absorbed. Cover the pan with its lid and set aside for three minutes. Sprinkle with chopped fresh Cilantro if desired and serve.

Test Method to Determine PGA (Propylene Glycol Alginate) & Protein/Starch Complexing Efficiency in the 'Regrind' from Pasta "Scrap"

Equipment & Reagents
1. Electric Kettle to boil the water.
2. Balance (0.01 g Sensitivity).
3. Distilled Water.
4. Sample Weighing boats.
5. Beakers (250 ml).
6. Glass mixing rods.
7. Mini sieves (150 mesh) to collect and weigh gelatinized/cooked 'regrind'.
8. Infrared Moisture Balance and tongs to handle sample dishes.
9. Timer (minutes/seconds)

Procedure:

Mill the pasta regrind/scrap and sift using the standard sieves. Weigh 10.00 grams regrind sample in to a clean 250 ml beaker.

In the electric kettle heat the distilled water and bring to boil.

Pour the boiling water on to the regrind in the beaker to the 100 ml mark and mix well with glass rod.

Start the three minute timer.

Mix the contents every 30 seconds to facilitate hydration/cooking (gelatinization)

At the end of three minutes, mix and pour the contents into the weighed sieve and collect the water in a clean/dry beaker.

Let water drain for 3 minutes.

Weigh the sieve containing cooked pasta product and beaker containing drained water and record the weights.

Calculate % yield.

Analyze % solids in the drained water using the Moisture Balance.

Calculate weight % cooking loss.

In the following experiment, pasta food compositions were prepared containing 0.03 weight percent PGA in the Invention samples, and no PGA in the Control samples. The cooking losses were measured and averaged over two trails and reported as the % Solids Loss. The following pasta products, made from semolina, were ground and sized to the same granulation as that of commercial "Cream of Wheat", and then cooked and measured for cooking loss as described above.

Invention=7.00 wgt. % Solids Loss

Control=9.68 wgt. % Solids Loss

CoW=15.66 wgt. % loss (This is commercially available 'Cream of Wheat'—Quick Cooking)

Blood Sugar Testing

Effect of PGA-containing food on Blood Glucose Levels in a Type 2 Obese

Patient: (average of two tests)

TABLE 1

| BLOOD GLUCOSE, in mg/dL - finger prick test | | | | |
| --- | --- | --- | --- | --- |
| Hours after Meal | Invention | Control | +/− | % |
| 0 | 104 | 95 | +9 | +9.47 |
| 1 | 226 | 267 | −41 | −15.36 |
| 3 | 118 | 195 | −77 | −39.49 |
| 5 | 61 | 93 | −32 | −34.4 |

The patients consumed the same mass (420 grams) of cooked (as described above) pasta product with PGA (Invention) and without PGA (Control). On each test day (four different days) the patient was overnight fasting. Blood glucose determination was made before the meal (breakfast) each day. This was a double crossover study, i.e., Invention meal one day, and Control meal the next day and repeated this order for the third and fourth days. No other items such as sauce, side dishes, coffee or tea were consumed for the entire 5-hour test periods.

The data in Table 1 were obtained using the ACCU CHECK, Instant GLUCOMETER. This is manufactured in Germany by Boehringer Maneheim, GmbH for Roche Diagnostics, Boehringer Maneheim Corporation, Indianapolis, Ind. 46250. The procedure for determining the glucose in the blood using this GLUCOMETER was as follows:

1. Calibrate the instrument using the standard calibration strip that comes with the instrument.
2. Insert the test strip following the direction.
3. Clean/Wash hands with soap, wipe dry.
4. Wipe the fingertip with alcohol pad to disinfect.
5. Using the 'lancet' that comes with instrument prick the tip of the sterilized finger.
6. Transfer drop of the blood on to the testing part of the strip as per the directions.
7. Press start button.
8. The analysis starts as indicated by the count down timer (60 seconds).
9. At the end of 60 seconds digital read flashes on the display screen. Number shown is mg Glucose per Deci-Liter (mg/DL)

These are universally accepted units of blood glucose measurements. In healthy (non-obese) individuals, the blood glucose is around 110 mg/DL.

A review of the results in Table 1 illustrates that the inventive food composition resulting from the reduced cooking losses of pasta containing PGA produced significantly lower blood glucose levels in the obesity patient at 1 hour, 3 hour and 5 hour tests relative to the blood glucose levels at the same time periods for a obesity patient who had consumed conventional (high cooking loss) pasta without PGA. This occurred despite the fact that the initial blood glucose readings (in mg/dl) at time zero showed a higher value (104 mg/dl) for the patient who consumed the Inventive pasta than the value (95 mg/dl) for the patient who consumed the Control pasta.

It is well known in the medical and dietary sciences that hunger and desire ti eat are triggered by blood glucose levels. Reduction of blood glucose levels reduces the impulse to consume food, resulting in altered eating behavior patterns. These changes in eating behavior patterns can subsequently and directly produce weight loss in the individual.

Thus, there is provided by the present invention a food composition useful in a dietary treatment of overweight individuals or patients with obesity whereby the blood glucose levels can be reduced relative to blood glucose levels in a obesity patient not exposed to the present invention. The result of this reduction in blood glucose level is a reduction in the person's desire, need or impluse to eat more, whereby weight gain is slowed or stopped and weight reduction is achievable.

Also presented is a method of reducing the glycemic index in a patient suffering obesity, said method comprising the steps of including in the diet of said obese patient a glycemic index reducing amount of a PGA-containing food composition with reduced cooking losses relative to conventional food composition without PGA.

Cooking losses in pasta can be reduced according to the present invention by reducing the cooking loss after being cooked in boiling water comprising the steps (a) preparing a pasta dough consisting of wheat flour, water and from 0.01 to about 2.0 weight percent propylene glycol alginate; (b) cooking said pasta by, for example, placing in boiling water for a time sufficient to increase the percent weight gain due to hydration relative to similarly cooked pasta without propylene glycol alginate. The pasta dough can be optionally shaped and dried to form a pasta after step (a) and before step (b).

A "glycemic index reducing amount" of PGA in the present invention is an amount equal to or greater than about 0.01 wgt % PGA in the food composition. No upper limit on the amount of PGA is established according to the present invention but an amount exceeding about 2.0 wgt % may become less desirable based on cost, texture, mouth feel, flavor alteration or other consumer preferences.

Thus, a preferred amount of PGA in pasta is from about 0.01 to about 2.0 wgt %, and a more preferred amount is from 0.35 to 1.25 wgt % PGA in the pasta. Preferred amounts in other starch-containing food compositions, such as rice, corn, etc can vary but are readily determined without undue experimentation. The amount of PGA or other hydrophilic agent herein useful in the present invention will vary with the source of the starch. Cornstarch granules are very small compared to potato starch granules. Starch granules can vary from 2 microns to 100 microns. Small diameter starch granules will generally require more PGA or other agent in the present invention because they have more surface area and thus require more PGA per unit mass.

Similarly, "a glycemic index reducing amount of a food composition" herein means any amount of a food composition containing any amount of an agent selected from the group consisting of propylene glycol alginate, glycerol monostearate, sodium stearoyl lactylate, D-glucose 3-stearate, methyl alpha-D-glucoside 6-stearate, sucrose monostearate, sorbitan tetrastearate, stearoyl-2-lactylate, sodium stearoyl fumarate, polyoxyethylene stearate, and stearyl monoglyceride citrate sufficient to reduce the glycemic index of a obesity patient or a person exhibiting abnormally high blood glucose levels.

The PGA is believed to act as a hydrophilic agent in the process of treating the starch. Alternative hydrophilic agents useful in the present invention can be selected from the group consisting of glycerol, sugar alcohol, starch hydrolysate, corn syrup, dextrose syrup, glycerol monostearate, sodium stearoyl lactylate, D-glucose 3-stearate, methyl alpha-D-glucoside 6-stearate, sucrose monostearate, sorbitan tetrastearate, stearoyl-2-lactylate, sodium stearoyl fumarate, polyoxyethylene stearate, and stearyl monoglyceride citrate and the like to prevent starch retrogradation in the cooked pasta product.

It is to be understood that the reactants and components referred to by chemical name anywhere in the specification or claims hereof, whether referred to in the singular or plural, are identified as they exist prior to coming into contact with another substance referred to by chemical name or chemical type. It matters not what chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together either in performing a desired chemical reaction or in forming a desired composition. Accordingly, even though the claims hereinafter may refer to substances, components and/or ingredients in the present tense ("comprises", "is", etc.), the reference is to the substance, components or ingredient as it existed at the time just before being blended or mixed with one or more other substances, components and/or ingredients in accordance with the present disclosure. The fact that the substance, components or ingredient may have lost its original identity through a chemical reaction or transformation during the course of such blending or mixing operations is thus wholly immaterial for an accurate understanding and appreciation of this disclosure and the claims thereof.

At numerous places throughout this specification, reference has been made to a number of U.S. Patents. All such cited documents are expressly incorporated in full into this disclosure as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A method of reducing the glycemic index in an overweight or obese person, said method comprising the step of including in the diet of said overweight or obese person a glycemic index reducing amount of a cooked food composition containing at least 0.01 wgt % of propylene glycol alginate or pharmaceutically acceptable salts thereof and gelatinized starch, whereby the glycemic index of said person is reduced.

2. A method of reducing the glycemic index in an overweight person or patient suffering obesity, said method comprising the step of including in the diet of said overweight person or obese patient a glycemic index reducing amount of a cooked food composition comprising at least 0.01 wgt % of a material selected from the group consisting of glycerol monostearate, sodium stearoyl lactylate, D-glucose 3-stearate, methyl alpha-D-glucoside 6-stearate, sucrose monostearate, sorbitan tetrastearate, stearoyl-2-lactylate, sodium stearoyl fumarate, and polyoxyethylene stearate, whereby the glycemic index of said person or patient is reduced.

3. A method for providing nutrition to an overweight or obese patient while substantially reducing said patient's blood glucose level, said method comprising the step of enterally administering to the patient a meal comprising a blood glucose level reducing amount of a cooked food composition comprising at least 0.01 weight percent propylene glycol alginate, or pharmaceutically acceptable salts thereof and gelatinized starch.

4. A method for treating weight gain of a person, said method comprising the step of enterally administering to the person a food composition prepared by a method comprising;
   (a) preparing a first food composition consisting of a material selected from the group consisting of wheat, tapioca, barley, oat, potato, rice, corn flour, and mixtures thereof, water and at least 0.01 weight percent propylene glycol alginate, or pharmaceutically acceptable salts thereof;
   (b) cooking said first food composition to increase the percent weight gain of the first food composition due to hydration relative to the percent weight gain of a cooked similar second food composition without propylene glycol alginate; and
   (c) consumption of said first food composition by the person whereby weight gain of the person is less than the person's weight gain after consumption of a comparable amount of said second food composition.

5. A method that controls the glucose released into the blood of an overweight person, said release initiated by enzymatic action in said overweight person, said method comprising the step of enterally administering to the person a meal comprising a blood glucose level reducing amount of a cooked food composition comprising at least 0.01 weight percent propylene glycol alginate, or pharmaceutically acceptable salts thereof and gelatinized starch.

6. A method for controlling during starch hydrolysis the membrane structure of a starch granule in a cooked food composition for consumption by an overweight or obese person said method comprising the incorporation into said food composition of a therapeutically effective amount of propylene glycol alginate or pharmaceutically acceptable salts thereof and gelatinized starch, followed by the consumption of said food composition by said person.

7. A method for reducing the glycemic index of a person, said method comprising the step of enterally administering to the person a food composition prepared by a method comprising;
   (a) preparing a first food composition consisting of a material selected from the group consisting of wheat, tapioca, barley, oat, potato, rice, corn flour, and mixtures thereof, water and at least 0.01 weight percent propylene glycol alginate, or pharmaceutically acceptable salts thereof;
   (b) cooking said first food composition to increase the percent weight gain of the first food composition due to hydration relative to the percent weight gain of a cooked similar second food composition without propylene glycol alginate; and
   (c) consumption of said first cooked food composition by the person, whereby the glycemic index of the person is less than the person's glycemic index after consumption of said second food composition.

* * * * *